United States Patent
Johnson et al.

(10) Patent No.: US 9,772,267 B2
(45) Date of Patent: Sep. 26, 2017

(54) MICROWAVE-ASSISTED BITUMEN EXTRACTION WITH VACUUM-ASSISTED SEDIMENT FILTRATION

(71) Applicants: Adam P. Johnson, The Woodlands, TX (US); Mauro Lo Cascio, Houston, TX (US); Samer F. Farjo, Spring, TX (US)

(72) Inventors: Adam P. Johnson, The Woodlands, TX (US); Mauro Lo Cascio, Houston, TX (US); Samer F. Farjo, Spring, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 68 days.

(21) Appl. No.: 14/878,029

(22) Filed: Oct. 8, 2015

(65) Prior Publication Data

US 2016/0109340 A1    Apr. 21, 2016

Related U.S. Application Data

(60) Provisional application No. 62/066,203, filed on Oct. 20, 2014.

(51) Int. Cl.
*G01N 1/44*   (2006.01)
*G01N 33/28*  (2006.01)
(Continued)

(52) U.S. Cl.
CPC .............. *G01N 1/44* (2013.01); *C10G 1/04* (2013.01); *C10G 1/045* (2013.01); *G01N 1/04* (2013.01);
(Continued)

(58) Field of Classification Search
CPC ........................................................ G01N 1/44
See application file for complete search history.

(56) References Cited

U.S. PATENT DOCUMENTS

| | | | |
|---|---|---|---|
| 4,136,014 A | 1/1979 | Vermeulen et al. | |
| 4,240,897 A | 12/1980 | Clarke | |

(Continued)

FOREIGN PATENT DOCUMENTS

| | | |
|---|---|---|
| CA | 1293943 | 7/1988 |
| CA | 1308378 | 9/1989 |
| CA | 2611533 | 5/2009 |

OTHER PUBLICATIONS

Liu, W., et al., (2012), "Extracting Bitumen From Inner Mongolia Oil Sand Using Several Common Surfactants", Advanced Materials Research, vol. 550-553, pp. 1739-1742.

(Continued)

*Primary Examiner* — Ryan Walsh
(74) *Attorney, Agent, or Firm* — ExxonMobil Upstream Research Company—Law Department

(57) ABSTRACT

Method for characterizing a heavily biodegraded oil sand ore sample by microwave-assisted bitumen extraction. Vacuum-filtration of solvent-extracted bitumen and sediments provides a means to recover sediment fines down to a particle size of 0.8 μm, which is the analytical requirement for accurate mineralogical analysis of the clay mineral fraction. The method may be completed in hours, making it suitable for "just-in-time" analyzes at the mine site. The recovered sediment and sediment fines are suitable for characterization using traditional analytical techniques to understand mineralogy, petrology, and reservoir properties.

20 Claims, 1 Drawing Sheet

(51) Int. Cl.
| | |
|---|---|
| *G01N 30/06* | (2006.01) |
| *H01J 49/04* | (2006.01) |
| *G01N 1/04* | (2006.01) |
| *C10G 1/04* | (2006.01) |
| *G01N 30/02* | (2006.01) |

(52) U.S. Cl.
CPC ......... *G01N 30/06* (2013.01); *G01N 33/2835* (2013.01); *H01J 49/0468* (2013.01); *G01N 2030/027* (2013.01)

(56) References Cited

U.S. PATENT DOCUMENTS

| | | | |
|---|---|---|---|
| 4,419,214 | A | 12/1983 | Balint et al. |
| 4,954,240 | A * | 9/1990 | Eidt, Jr. .................. C10B 55/00 208/50 |
| 7,629,497 | B2 | 12/2009 | Pringle |
| 7,652,708 | B2 | 1/2010 | Nakajima |
| 2007/0137852 | A1 | 6/2007 | Considine et al. |
| 2007/0137858 | A1 | 6/2007 | Considine et al. |
| 2009/0139716 | A1 | 6/2009 | Brock et al. |
| 2010/0193404 | A1 | 8/2010 | Yeggy et al. |
| 2011/0025336 | A1 | 2/2011 | Forgang et al. |
| 2011/0114470 | A1 | 5/2011 | Cha et al. |
| 2011/0127197 | A1* | 6/2011 | Blackbourn ............. C10G 1/04 208/390 |
| 2012/0048783 | A1* | 3/2012 | Painter ................... C10G 1/04 208/390 |

OTHER PUBLICATIONS

Robinson, J., et al., (2014), "Microwave Processing of Oil Sands and Contribution of Clay Minerals", Fuel 135, pp. 153-161.

Wang, T., et al., (2014), "Solvent Extraction of Bitumen From Oil Sands", Energy & Fuels, vol. 28, pp. 2297-2304.

Bosisio, R.G. et al. (1977), "Experimental results on the heating of Athabasca tar sand samples with microwave power," *Journal of Microwave Power* 12 (4), pp. 301-307.

Brannegan, D. et al. (2011), "Extraction techniques leveraging elevated temperature and pressure, Sample Preparation and of Pharmaceutical Dosage Forms," Challenges and Strategies for Sample Preparation and Extraction, B. Nickerson, ed., pp. 93-128.

Eskilsson, C.S. et al. (2000), "Analytical-scale microwave-assisted extraction," *Journal of Chromatography A* 902, pp. 227-250.

Ganzler, K. et al. (1986), "Microwave Extraction, A Novel Sample Preparation Method for Chromatography," *Journal of Chromatography* 371, pp. 299-306.

Letellier, M. et al. (1999), "Focused microwave-assisted extraction of polycyclic aromatic hydrocarbons and alkanes from sediments and source rocks," *Organic Geochemistry* 30, pp. 1353-1365.

Mutyala, S. et al. (2010), "Microwave applications to oil sands and petroleum: A review," *Fuel Processing Technology* 91, pp. 127-135.

Peng, Z. et al. (2011), "Evaluating the performances of accelerated-solvent extraction, microwave-assisted extraction, and ultrasonic-assisted extraction for determining PCBs, HCHs and DDTs in sediments," *Chinese Journal of Oceanology and Limnology* 29(5), pp. 1103-1112.

Renoe, B. (1994), "Microwave assisted extraction," *American Laboratory*, pp. 34-40.

Wang, P. et al. (2010), "Evaluation of Soxhlet Extraction, accelerated solvent extraction and microwave-assisted extraction for the determination of polychlorinated biphenyls and polybromnated diphenyl ethers in soil and fish samples," *Analytica Chimica Acta* 683, pp. 43-48.

Zuloaga, Q. et al. (1998), "Comparison of accelerated solvent extraction with microwave-assisted extraction and Soxhlet for the extraction of chlorinated biphenyls in soil samples," *Trends in Analytical Chemistry* 17(10), pp. 642-647.

* cited by examiner

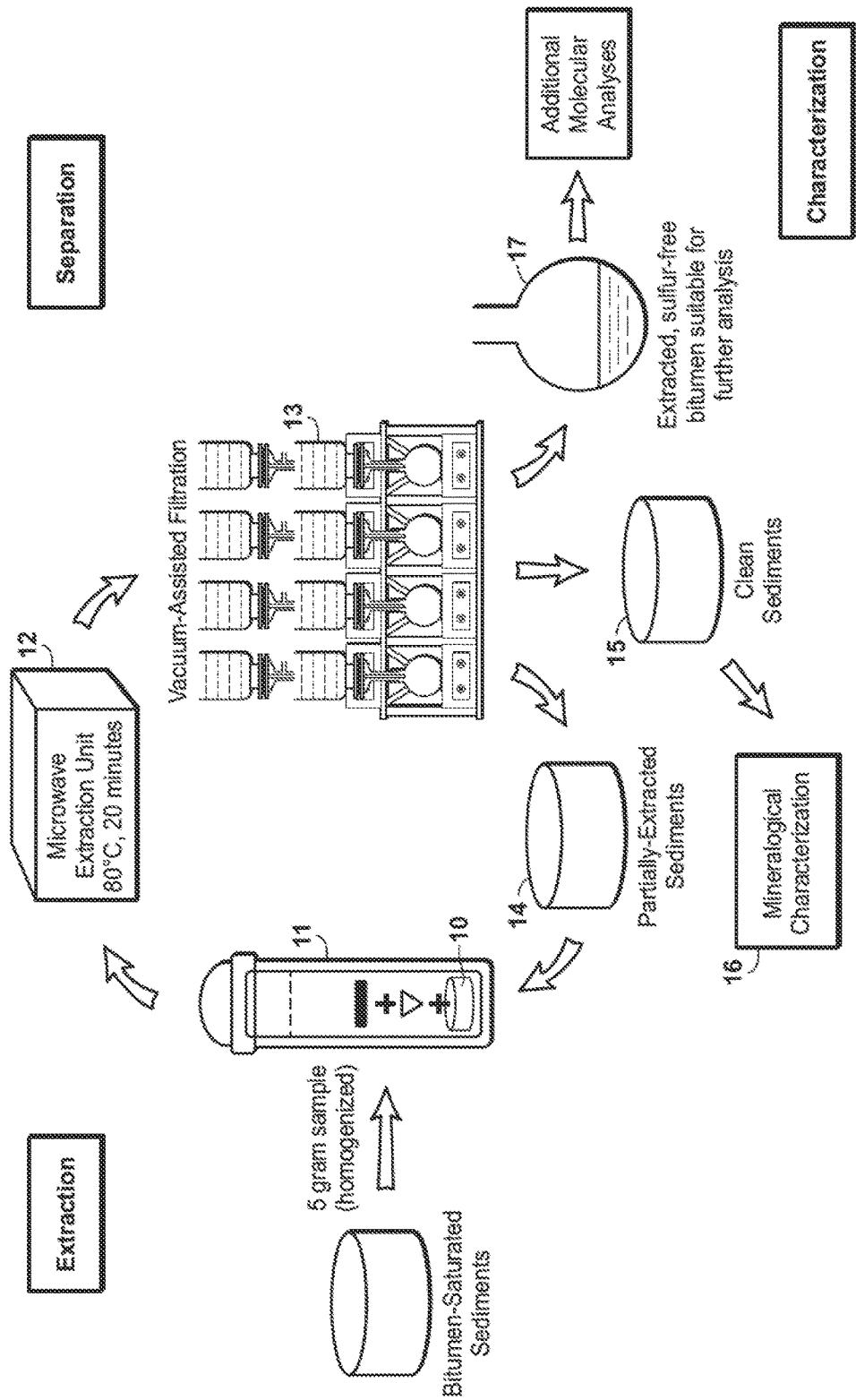

MICROWAVE-ASSISTED BITUMEN EXTRACTION WITH VACUUM-ASSISTED SEDIMENT FILTRATION

CROSS-REFERENCE TO RELATED APPLICATIONS

This application claims the benefit of U.S. Provisional Application Ser. No. 62/066,203, filed Oct. 20, 2014, entitled MICROWAVE-ASSISTED BITUMEN EXTRACTION WITH VACUUM-ASSISTED SEDIMENT FILTRATION, the disclosure of which is incorporated herein by reference.

FIELD OF THE INVENTION

This disclosure relates generally to the field of geophysical prospecting for hydrocarbons and, more particularly, to oil sand evaluation. Specifically, the disclosure relates to a method for microwave-assisted extraction of bitumen from oil sands for characterization of the oil sands.

BACKGROUND OF THE INVENTION

Geochemical analyses of bitumen and sediments from highly biodegraded oil sand samples presents substantial business and analytical challenges for routine characterization. Access to data from rapid, reliable characterization of oil sands bitumen and sediment is critical to daily operations and business decisions. Some laboratories may lack the capability or turn-around time to adequately provide data on a daily basis. The nature of the samples prevents the use of traditional mineralogical analyses, such as optical microscopy, x-ray diffraction, and x-ray fluorescence, until the sediments of interest are isolated from the bitumen in the sample. Conventional geochemical extraction techniques are limited by the high level of bitumen saturation in oil sands samples and the decreased solubility of the asphaltene-rich bitumen in traditional organic solvents, requiring substantial time and solvent volume requirements in order to provide quantities of extracted sediment suitable for characterization.

Standard geochemical extraction techniques, such as Soxhlet or Soxtec extractions, are limited in their extraction efficiency by the azeotropic boiling point of the solvent mixture under normal conditions. High levels of bitumen saturation (e.g., greater than 1%) in oil sand samples, combined with the decreased extraction efficiency of conventional techniques, can require substantial time (e.g., days to weeks) and solvent requirements (e.g., greater than 1 liter) in order to provide quantities of extracted sediment suitable for characterization (e.g., greater than 10 grams). Conventional extraction techniques typically lose clay minerals and fines (e.g., less than 10 µm) during the extraction process; this fraction of sediment is critical since fines content may be a controlling factor when determining overall bitumen extractability during mining processes. Access to data from this fraction will be critical in order to address daily operation and business-related decisions.

Prior publications have compared conventional solvent extraction techniques against microwave extraction techniques and have shown that microwave techniques typically utilize lower solvent volumes and reduced extraction times. For example, application of microwave technology at analytical-scale extractions were first proposed in the mid-1980's and showed comparable-to-improved recoveries relative to traditional analytical extraction techniques, although solvent choice was a strong driver for overall recovery of given compounds. See e.g., Ganzler, K., Salgo, A., Valko, K., "Microwave Extraction: A Novel Sample Preparation Method for Chromatography," *Journal of Chromatography,* 371, 299-306 (1986). The largest advantage to microwave extraction techniques was understood to be the substantially-reduced solvent volumes (e.g., up to 100 times less) and reduced extraction times. Additional work included extraction of polycyclic aromatic compounds and hydrocarbons from source rocks, which showed 88-96% recovery of spiked rock samples compared to Soxhlet techniques, while extraction from natural rock samples showed increased extraction yields, from 86-119%, depending on compound type. See e.g., M Letellier, H Budzinski, J Bellocq, J Connan, "Focused microwave-assisted extraction of polycyclic aromatic hydrocarbons and alkanes from sediments and source rocks", *Organic Geochemistry* 30, 1353-1365, ISSN 0146-6380 (November, 1999). More recent work has focused on the extraction of chlorinated pollutants from soils and tissues using microwave techniques relative to more traditional Soxhlet or accelerated solvent extraction techniques; in all cases microwave extractions were shown to have increased recoveries, shorter extraction times and lower solvent volumes when appropriate solvents (appropriate for what is being extracted) are utilized. See e.g., Wang, Pu; Zhang, Qinghua; Wang, Yawei; Wang, Thanh, et al., "Evaluation of Soxhlet Extraction, accelerated solvent extraction and microwave-assisted extraction for the determination of polychlorinated biphenyls and polybromnated diphenyl ethers in soil and fish samples," *Analytica Chimica Acta* 683, 43-48 (2010). See also, Zhang, Peng, Linke, G E, Zhou, Chuanguang, et al., "Evaluating the performances of accelerated-solvent extraction, microwave-assisted extraction, and ultrasonic-assisted extraction for determining PCBs, HCH's and DDT's in sediments." *Chinese Journal of Oceanology and Limnology* 29, No. 5, 1103-1112 (2011). Overall, the literature supports the proposition that, for the particular substances they were being applied to, microwave extraction provides overall increased extraction recoveries, efficiencies, and reduced solvent volumes without appreciable degradation of the compounds of interest. However, little work has focused on the direct analysis of petroleum hydrocarbons, in particular oil sands bitumen composition, using microwave extraction techniques.

The application of microwave technology to oil sand bitumen extractions was proposed as early as the late 1970's to 1980's, although these proposals focused on the upgrading of heavy oil sands bitumen to more refinable products. For example, a microwave heating system was utilized to yield up to 86% recovery of initial bitumen composition, with the remaining waste composed of 1-2% carbon graphite and various hydrocarbon gases, including hydrogen, acetylene, methane carbon monoxide, and carbon dioxide. See R. G. Bosisio, J. L. Cambon, C. Chavarie, D. Klvana, "Experimental results on the heating of Athabasca tar sand samples with microwave power," *Journal of Microwave Power* 12 (4) 301-307 (1977). However, these experiments were performed in a solvent-free system and relied only on in-situ sample water for heating. U.S. Pat. No. 4,419,214 describes irradiated oil sands, shale rock, and lignite under pressure and utilized gaseous or liquid $CO_2$ and/or other vapor hydrocarbon solvents in high frequency microwaves. Canadian Patent Nos. 1,293,943 and 1,308,378 utilized aqueous solvents to show separation of oil sand bitumen from mineral phases at both elevated (e.g., 500° C.) and low (e.g, less than 100° C.) temperatures. However, these Canadian patents describe bitumen separation into an upper bitumen fraction and a lower mineral fraction, describing each layer merely as containing a greater proportion of either bitumen or mineral than the other layer. A series of experiments in U.S. Pat. No. 4,419,214 suggest that anywhere from 20% to over 90% of tar was removed from mineral sands during the process.

More recent work in the past decade has again focused on technologies and methods that utilize microwave energy to both increase heavy oil production and to degrade heavy oils to more refinable products. For example, U.S. Patent Application Publication No. 2007/0137852 proposed a technology that would extract hydrocarbon fuel products like kerogen oil and/or gas from solid hydrocarbon using a combination of electrical energy that was provided by an electromagnetic field generator to critically heat $CO_2$, $N_2O$ or $O_2$ in subsurface heavy oil accumulations, producing a less viscous vapor, liquid, or dissolved oil phase that would be pumped back to the surface. Similar techniques disclosed in U.S. Patent Application Publication Nos. 2009/0139716 and 2011/0253362 suggest using microwave energy to help mobilize subsurface accumulations of heavy oil, either by direct heating using field-wide wells with electromagnetic heating (as in U.S. Patent Application No. 2009/0139716) or by using microwave energy to heat production water pumped into subsurface reservoirs (as in U.S. Patent Application No. 2011/0253362) with the goal of, in both cases, reducing oil viscosity to increase hydrocarbon recovery. U.S. Pat. No. 7,629,497 has suggested development of large-scale microwave technologies that would degrade petroleum-containing compounds such as tires, plastics, etc. or that could be used for the recovery of subsurface heavy oils, oil shales, or tar sands. U.S. Patent Application No. 2011/0114470 describes a technique for application at surface mine sites, where microwave energy is used to dry and refine hydrocarbons to a more refinable state, with bitumen recoveries that range from 50-80%.

Despite the amount of research into microwave technology in the separation of oil sands, these separation recoveries using these techniques have only been qualitatively reported and are unlikely to be robust enough for geochemical or mineralogical characterization of the resulting bitumen or mineralogy despite extensive analytical research in other fields that suggests microwave extractions may be more robust than traditional extraction techniques. Therefore, there remains a need for reliable and relevant sample preparation methods to address questions related to daily mining operations, such as analytical extraction technique for oil sands.

SUMMARY OF THE INVENTION

In one embodiment, the invention is an oil sand characterization method, comprising: (a) heating a mixture of an oil sand ore sample and an organic solvent that may or may not have a dipole moment in a microwave reaction vessel at a temperature not to exceed 130° C.; (b) after microwaving for a preselected length of time, using vacuum-assisted filtering on resulting bitumen-saturated solvent to collect extracted bitumen separated from sediment and sediment fines; and (c) analyzing the separated sediment and sediment fines for mineral characterization.

BRIEF DESCRIPTION OF THE DRAWINGS

The advantages of the present invention are better understood by referring to the following detailed description and the attached FIGURE, which is a flow chart, showing basic steps in one embodiment of the present inventive method.

The invention will be further described in connection with example embodiments. However, to the extent that the following detailed description is specific to a particular embodiment or a particular use of the invention, this is intended to be illustrative only, and is not to be construed as limiting the scope of the invention. On the contrary, it is intended to cover all alternatives, modifications and equivalents that may be included within the scope of the invention, as defined by the appended claims.

DETAILED DESCRIPTION OF EXAMPLE EMBODIMENTS

In order to provide reliable and relevant sample preparation to address questions related to daily mining operations, any analytical extraction technique for oil sands samples should address a number of criteria: (a) it needs to have a high extraction efficiency in order to allow the extraction of large volumes of bitumen and provide adequate sediment mass for routine mineralogical analyses; (b) the extraction technique should use the minimal volume of organic solvent necessary in order to minimize potential environmental impacts; (c) it needs to be relatively simple and fast for rapid turn-around, on the order of a few hours, to provide samples for "just-in-time" analyses at the mine site; and (d) the technique must not alter either the mineralogical or geochemical composition of the sample so that prepared samples are reflective of the composition of the native sample. For purposes of the present document, including the claims, the term "oil sand(s)" will be understood to include all variations of tar sands, heavy oils, and oil shale.

The present invention utilizes a combination of microwave-assisted extraction techniques and vacuum-assisted sediment filtration to provide a means to 1) extract bitumen and sediment from oil sand samples and 2) provide a means to separate the solvent-extracted bitumen from sediment and sediment fines to (e.g., particulates with a diameter of less than or equal to 0.8 µm). Microwave-assisted extraction can increase bitumen extraction efficiency by increasing the extraction temperature from the azeotropic solvent boiling point at normal conditions (e.g., 40-45° C.) to 80° C. by using sealed reaction chambers that can be run above normal atmospheric pressures. Elevated solvent temperatures can increase bitumen solubility and can therefore decrease the solvent volume requirements needed to extract suitable masses of sediment.

The present method utilizes a standard organic solvent mixture, similar to the solvents that have previously been used in conventional, low-temperature (non-microwave) extraction applications for extraction of organics from particulate matter. For purposes of this application and the appended claims, the term organic solvent will not include the aforementioned atypical solvents such as critical CO2 or N2 gas, but will include all non-aqueous carbon-based solvents that may or may not contain a dipole moment. For example, in some embodiments the organic solvent may comprise a mixture of dichloromethane and methanol (DCM:MeOH). The mixture may be used in a volume: volume ratio of DCM:MeOH of from about 1:99 to 99:1, or from about 5:95 to about 95:5, or from about 75:25 to about 25:75, or about 50:50. In some embodiments, the mixture may be used in a volume:volume ratio of DCM:MeOH of from about 80:20 to 99:1, or from about 85:15 to 95:5, or from about 97:13 to 92:18, or about 90:10.

The use of organic solvents will increase overall recovery due to the miscibility of the various petroleum-related compounds in organic solvent compared to aqueous or atypical solvent phases. The use of organic solvents, in combination with the elevated temperatures and extraction efficiencies imparted by microwave extraction techniques, will provide a robust analytical-scale extraction technique that is suitable for quantification and both molecular and mineralogical characterization. To date, there appear to be no vendor or service provider or any publication describing utilizing the techniques disclosed herein for extracting heavy oil bitumen using a method that provides over 95% recovery.

Steps of a laboratory procedure for implementing one exemplary embodiment of the present inventive method are described with reference to the schematic flow chart FIGURE, which displays the process in three stages: extraction, separation, and characterization. In the extraction stage, bitumen ore may be saturated in solvent and heated above the solvent aziotrope using microwave radiation. Typical elements and specifications for this stage may include: (1) the sample 10; (2) solvent, such as 75 ml 90:10 (v:v) DCM:MeOH; (3) carbide heating element; (4) magnetic stirrer; (5) Teflon reaction liner; (6) ceramic reaction vessel; and (7) pressure-safety cap. In the separation stage, sediments may be filtered from extracted bitumen using a vacuum-assisted filtration assembly. Elemental sulfur may be removed from extracted bitumen using activated copper and heating. Typical elements and specifications for this stage may include: (1) a water aspiration vacuum assembly; (2) a borosilicate glass filtration assembly; (3) heating elements; (4) 0.2 micron filter paper; and (5) activated copper. In the characterization stage, extracted elemental sulfur-free bitumen is characterized using chromatographic techniques. Bitumen-free sediments are characterized using routine mineralogical and/or core analyses. These stages are next described in more detail.

Fresh or preserved oil sand ore samples are weighed, recorded, and placed into the microwave reaction vessels with solvent, such as 75 mL of a 90:10 dichloromethane/methanol solvent mixture, with a carbide heating element and Teflon magnetic stirrer. Samples are sealed (step 11), placed in the microwave extraction unit, and raised to 80° C. solvent temperature for 20 minutes using microwave radiation as the heating source (step 12). The microwave unit may be a commercially available apparatus designed for laboratory-based digestions and extractions using microwave radiation. Samples are cooled, opened, and the resulting bitumen-saturated solvent is carefully decanted into the vacuum-assisted filtration assembly (step 13) to collect the extracted bitumen from the sediment and sediment fines on a pre-selected glass fiber filter of a previously selected pore size. The process is repeated (step 14) twice more, with fresh solvent added to the sample, extracted at 80° C. for 20 minutes, and the bitumen-saturated solvent decanted into the filtration system. During the final (3rd) extraction, the reaction vessel is rinsed with fresh solvent to remove all remaining sediment and sediment fines into the vacuum assembly. The samples are filtered until dry, at which time the collected fines (15) are transferred to appropriate sample containers and delivered to the necessary labs for additional mineralogical characterization (step 16). The resulting bitumen-saturated solvent collected during the extraction may be mildly heated in the presence of copper in the filtration assembly to remove trace levels of elemental sulfur that may have been extracted with the bitumen (step 17). The extracted bitumen is suitable for characterization using chromatography or mass spectroscopy to understand the molecular composition. It should be noted that the specificity provided with reference to the FIGURE is for an exemplary embodiment of the invention, and that, for example, other solvents and amounts may be used as known by those skilled and the art.

Although the filtration protocol is a wet chemistry laboratory technique that has been applied to samples from a number of different fields outside of geochemistry, and microwave extraction has been heavily utilized in food extractions, digestions, and synthesis reactions for several decades, the value of the present disclosure may be apparent from the fact that microwave extraction and subsequent sample filtration have never been applied to heavy oil and bitumen samples to solve the very real technical problem of providing quantitative, analytical separations of bitumen and sediments for advanced molecular and mineralogical characterization of oil sand deposits. Oil sands have been commercially attractive for decades, and traditional Soxhlet or Soxtec techniques have been used to characterize the deposits, for several years. It seems likely that it has not been previously appreciated or understood that there is a viable temperature range and extraction time range for microwave extraction to be applied to oil sand samples without negative effect on either bitumen geochemistry or sediment mineralogy.

Testing and research suggest that conventional extraction techniques (Soxhlet, Soxtec) typically have solvent-to-ore (volume/mass) ratios of up to 500:1 (v/m), while initial results from the present inventive method for microwave assisted extraction suggest solvent to ore ratios may be as low as 200:1 (v/m). For example, the present methods may utilize a solvent to ore ratio of less than 200:1 (e.g., 200 ml solvent per 1 g sample), or less than 100:1 (e.g., 100 ml solvent per 1 g sample), or less than 75:1 (e.g., 75 ml solvent per 1 g sample), or less than 50:1 (e.g., 50 ml solvent per 1 g sample), or less than 25:1 (e.g., 25 ml solvent per 1 g sample), or less than 20:1 (e.g., 20 ml solvent per 1 g sample). Decreased solvent volumes will lower costs associated with purchase, storage, and waste disposal. Decreased solvent waste volumes will minimize environmental impacts at mine sites where environmental concerns are already highly regulated, and will minimize potential safety-related issues with large solvent volume and disposal in remote lab environments.

Results obtained during the development of the present method for microwave-assisted extraction of oil-sand ore samples indicate that neither bitumen geochemistry nor sediment mineralogy were affected by accumulated microwave radiation dosage or absolute radiation levels provided that a maximum temperature is maintained throughout the extraction process. Preferably, the extraction temperature is less than 130° C., or less than 120° C., or less than 110° C., or less than 100° C., or less than 90° C., or less than 80° C., or less than 70° C., or less than 60° C. Increased clay mineral strain (e.g., about 50%) was observed between samples extracted at 130° C. compared to 80° C. However, no difference in clay mineral strain was observed with accumulated radiation dosages from 20-160 minutes exposure time. Further, hydrated clay minerals showed no effects from supercritical heating of interlayer water with increased extraction times (e.g., 20-160 minutes). Comparisons of microwave-extracted and conventional Soxhlet-extracted bitumen show consistent bitumen geochemical compositions (within analytical error) between the two techniques, including; residual total organic carbon (TOC) of the mineral phase, molecular characterization using whole oil gas chromatography, boiling point distributions, liquid chromatography, and diagnostic molecular ratios from saturate and aromatic parameters. These statements held true when microwave extraction temperatures were below 80° C.; above this temperature, variations in bitumen composition occur and are consistent with the previously cited mineralogical results.

The use of vacuum-filtration of solvent-extracted bitumen and sediments provides the means to recover sediment fines down to particle sizes less than 0.8 µm, which is the analytical requirement for accurate mineralogical analysis of the clay mineral fraction. Conventional solvent-extraction techniques are limited to 8-10 µm particle-size retention due to the use of the porous sample thimbles used in the extraction method; i.e., particles smaller than that will pass through the filter and not be retained. A vacuum-filtration assembly for the present invention can be equipped with any pore size filter in order to provide a wide range of particle sizes (e.g., less than 10 µm, or less than 9 µm, or less than 8 µm, or less than 7 µm, or less than 6 µm, or less than 5 µm) suitable for a number of mineralogical techniques. The vacuum-filtration assembly may be made of borosilicate glass, which allows easy assembly, disassembly, and cleaning of the components to ensure minimal risk of cross-sample contamination from one filtration to another. Use of a low-pressure water aspirator as the vacuum source provides suitable low-vacuum to drive rapid filtration of bitumen-saturated solvents and sediment fines without the need for explosion-proof glassware or vacuum pumps. The vacuum-filtration setup may also incorporate low-temperature heating mantles that allow the ability to heat filtered bitumen extracts as part of an elemental-sulfur removal process. Vacuum-assisted filtration can provide a recovery of clay minerals and fines up to 2.5 weight percent sample mass compared to zero recovery in conventional extraction techniques, allowing quantitative mineralogical analyses of the sample fraction that may drive business-critical daily operation decisions.

To summarize, microwave-assisted extraction, coupled with the vacuum-assisted sediment filtration, provides a number of specific benefits compared to current geochemical extraction techniques. Microwave-assisted extractions are faster than traditional Soxhlet or Soxtec techniques. Typical extractions can range from 2 to 12+ hours based on the organic richness of the sample, while microwave extractions can take as little as 2-4 hours to extract and separate bitumen from sediment. Microwave-assisted extractions have better extraction efficiency than traditional extraction techniques due to the elevated extraction temperatures (e.g., 80° C.) and utilize a lower solvent-to-ore ratio (200:1) than traditional techniques (500:1) due to the increased extraction efficiency. Microwave-assisted extractions are more environmentally friendly since they produce lower solvent volumes (per equivalent gram of sample) compared to traditional techniques. Microwave-assisted extractions can handle up to, for example, 16 separate 5-gram samples or up to 80 grams of a single ore sample per 2-4 hour extraction; traditional extraction techniques are limited by the number of available extraction systems since a separate system is required for each sample. As a result, microwave assisted extractions also take up less laboratory space. Vacuum-assisted filtration allows rapid collection of microwave-extracted sediment fines (to 0.8 µm for characterization—the sediment fraction less than that are typically lost during traditional extraction techniques due to the porous sample thimble used in the technique.

The foregoing description is directed to particular embodiments of the present invention for the purpose of illustrating it. It will be apparent, however, to one skilled in the art, that many modifications and variations to the embodiments described herein are possible. All such modifications and variations are intended to be within the scope of the present invention, as defined by the appended claims.

The invention claimed is:

1. An oil sand characterization method, comprising:
 (a) heating a mixture of an oil sand ore sample and an organic solvent to form a bitumen-saturated solvent, wherein the heating occurs in a microwave reaction vessel at a temperature not to exceed 90° C. for a period of time of less than 160 minutes and wherein the solvent to sample ratio in the mixture is less than 200 ml solvent per 1 cram sample;
 (b) after heating, using vacuum-assisted filtering on the bitumen-saturated solvent to collect extracted bitumen separated from sediment and sediment fines; and
 (c) analyzing the separated sediment and sediment fines for mineral characterization.

2. The method of claim 1, wherein the heating temperature is controlled to not exceed 80° C.

3. The method of claim 1, wherein the heating temperature is controlled to not exceed 70° C.

4. The method of claim 1, wherein the heating time is greater than 20 minutes.

5. The method of claim 1, further comprising repeating the method at least once with fresh solvent added to the sample.

6. The method of claim 1, wherein the organic solvent is a non-aqueous organic solvent that has a dipole moment.

7. The method of claim 1, wherein the microwave reaction vessel is a sealed reaction chamber, and is pressurized to above normal atmospheric pressure.

8. The method of claim 1, wherein the vacuum-assisted filtering uses a vacuum-filtration assembly with capability to filter out particles as small as 0.8 microns.

9. The method of claim 1, wherein the vacuum assist for the vacuum-assisted filtering is provided by a low-pressure water aspirator.

10. The method of claim 1, further comprising:
 taking the separated sediment and sediment fines at conclusion of step (b), adding more solvent, and repeating steps (a) and (b) one or more times until total weight percent recovery of bitumen is greater than 99 percent of the ore sample's total original bitumen mass.

11. The method of claim 1, wherein the method is performed at a mine site where the oil sand ore sample was obtained, and wherein the method is completed in less than eight hours.

12. The method of claim 1, further comprising analyzing the extracted bitumen, using chromatography or mass spectroscopy, to understand its molecular composition.

13. The method of claim 1, further comprising using the analysis from step (c) to evaluate commercial potential of the oil sand ore.

14. The method of claim 1, wherein recovered sediment fines are 0.8 µm or less in size.

15. The method of claim 1, wherein the organic solvent is a non-aqueous organic solvent that does not have a dipole moment.

16. The method of claim 1, wherein the vacuum-assisted filtering uses a vacuum-filtration assembly that is made of borosilicate glass.

17. The method of claim 1, wherein the solvent to sample ratio in the mixture is less than 100 ml solvent per 1 gram of sample.

18. The method of claim 1, wherein the solvent to sample ratio in the mixture is less than 25 ml solvent per 1 gram of sample.

19. The method of claim 1, wherein the organic solvent comprises a mixture of dichloromethane and methanol.

20. The method of claim 19, wherein the organic solvent comprises a volume:volume ratio of the dichloromethane to methanol of from 80:20 to 99:1.

\* \* \* \* \*